United States Patent
Ramón Azcón et al.

(10) Patent No.: US 9,170,227 B2
(45) Date of Patent: Oct. 27, 2015

(54) MULTI-ANALYTE SYSTEM AND METHOD BASED ON IMPEDIMETRIC MEASUREMENTS

(75) Inventors: Javier Ramón Azcón, Barcelona (ES); Francisco José Sánchez Baeza, Barcelona (ES); María Pilar Marco Colas, Barcelona (ES); Andrei Bratov Nikiforov, Barcelona (ES); Natalia Abramova, Barcelona (ES); Andrey Ipatov, Barcelona (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 473 days.

(21) Appl. No.: 13/516,186

(22) PCT Filed: Dec. 14, 2010

(86) PCT No.: PCT/ES2010/070824
§ 371 (c)(1),
(2), (4) Date: Aug. 21, 2012

(87) PCT Pub. No.: WO2011/073481
PCT Pub. Date: Jun. 23, 2011

(65) Prior Publication Data
US 2012/0309108 A1   Dec. 6, 2012

(30) Foreign Application Priority Data
Dec. 15, 2009 (ES) .................................. 200931164

(51) Int. Cl.
*G01N 27/327* (2006.01)
*G01N 33/538* (2006.01)

(52) U.S. Cl.
CPC .......... *G01N 27/3275* (2013.01); *G01N 33/538* (2013.01)

(58) Field of Classification Search
CPC ................................................. G01N 27/3275
See application file for complete search history.

(56) References Cited

U.S. PATENT DOCUMENTS 6,627,446 B1 * 9/2003 Roach et al. ..................... 436/43
2002/0028441 A1 3/2002 Hintsche et al.
(Continued)

FOREIGN PATENT DOCUMENTS

EP    1324019 A1    7/2003
ES    2307430 A1    11/2008
(Continued)

OTHER PUBLICATIONS

English translation; JP2005-90961; 29 pages.
(Continued)

*Primary Examiner* — Melanie Y Brown
(74) *Attorney, Agent, or Firm* — Blank Rome LLP

(57) ABSTRACT

The invention discloses a system for the simultaneous detection and/or quantification of various analytes in a sample or for the simultaneous detection and/or quantification of an analyte in various samples, comprising: a multi-electrode chip (10) comprising an array of microelectrodes (11a, 11b, 11c, 11d); a single-duct cell (20), comprising a groove (21) which accommodates the multi-electrode chip (10) and a duct (22) through which a fluid sample can sequentially flow through each of the microelectrodes (11a, 11b, 11c, 11d) of a multi-electrode chip (10) when the latter is inserted into the groove (21); and a multi-duct cell (30), comprising a groove (31) housing the multi-electrode chip (10) and several independent ducts (32a, 32b, 32c, 32d) through which several samples can pass independently through each electrode (11a, 11b, 11c, 11d) of the multi-electrode chip (10).

11 Claims, 4 Drawing Sheets

(56) References Cited

U.S. PATENT DOCUMENTS

| | | | |
|---|---|---|---|
| 2003/0134410 A1* | 7/2003 | Silva et al. | 435/287.2 |
| 2004/0001779 A1* | 1/2004 | Anderson et al. | 422/99 |
| 2006/0121500 A1* | 6/2006 | Bachman et al. | 435/6 |
| 2006/0160205 A1* | 7/2006 | Blackburn et al. | 435/287.2 |
| 2006/0194215 A1* | 8/2006 | Kronick et al. | 435/6 |
| 2008/0297169 A1 | 12/2008 | Greenquist et al. | |
| 2009/0221059 A1* | 9/2009 | Williams et al. | 435/287.2 |
| 2010/0193378 A1 | 8/2010 | Bratov et al. | |
| 2011/0003330 A1* | 1/2011 | Durack | 435/34 |

FOREIGN PATENT DOCUMENTS

| | | |
|---|---|---|
| JP | 2003-254906 A | 9/2003 |
| JP | 2005-90961 A | 4/2005 |
| WO | WO-2004044570 A1 | 5/2004 |

OTHER PUBLICATIONS

English translation; JP2003-254906; 14 pages.

International Search Report issued in PCT/ES2010/070824 on May 11, 2011.

Adrian, et al., A Multianalyte ELISA for Immunochemical Screening of Suflonamide, Fluoroquinolone and β-lactam Antibiotics in Milk Samples Using Class-Selective Bioreceptors, Anal Bioannal Chem (2008) 391:1703-1712.

Bataillard, et al., Direct Detection of Immunospecies by Capacitance Measurements, Anal. Chem. 1988, 60:2374-2379.

Van Gerwen, et al., Nanoscaled Interdigitated Electrode Arrays for Biochemical Sensors, Sensors and Actuators B 49, 1998, 73-80.

* cited by examiner

MULTI-ANALYTE SYSTEM AND METHOD BASED ON IMPEDIMETRIC MEASUREMENTS

This application is the U.S. national phase of International Application No. PCT/ES2010/070824, filed Dec. 14, 2010, which claims the benefit of Spanish Patent Application No. P200931164, filed Dec. 15, 2009.

OBJECT OF THE INVENTION

The main object of the invention is a system and method for the simultaneous detection and/or quantification of various analytes in a single sample or for the simultaneous detection and/or quantification of a single analyte in various samples.

BACKGROUND OF THE INVENTION

It is known that the impedance measurements make it possible to detect extremely small variations in the properties and chemical composition of the electrodes used for performing the measurement as well as of the surface thereof and the medium between them. This has allowed registering phenomena such as the formation of an antibody-antigen complex on the electrode surface (Bataillard, P. et al., Anal. Chem, 1988, 60, 2374). The first systems were unable to detect minor compounds and even less so at trace level in the samples analyzed. To increase the sensitivity of the technique and also to miniaturize the devices, transducers based on interdigitated electrodes were developed (P. van Gerwen et al., Sens. Actua. B, 1998, 49, 73). The use of these types of electrodes as chemical sensors by means of impedimetric measurements has been addressed in patents using various conceptions (WO2004044570) and essentially involves the immobilization of the compound which plays the role of receptor on the surface of the electrode and putting it in contact with the sample to be analyzed. If the complementary compound exists, it will bind to the receptor modifying the nature of the surface layer of the transducer and modifying the impedance thereof. The magnitude of change is proportional to the amount of compound bound to the transducer which in turn depends on the amount thereof present in the sample. The correlation can be performed with the impedance value at one or several interrogation frequencies or by adjusting the response according to the frequency to an equivalent circuit and correlating the value of one or more components with the analyte concentration.

Despite the above improvements, the systems still did not have the required sensitivity for the detection and quantification of compounds at trace level and even less so when involving compounds with low molecular weight (less than 1000 Dalton). A major improvement in the design of the transducers was the development of the interdigitated electrodes with insulating barriers between the conductive elements with a height of the order of the separation of the electrodes disclosed in patent ES2307430. This transducer device allows detecting low-molecular-weight compounds with a similar sensitivity to that of ELISA-type assays that use the same set of immunoreagents.

Along with the precedents in impedimetric sensor technology the precedent in multi-analyte-type immunochemical analysis techniques must be added. In general the multi-analyte methods are carried out by separation within each elementary immunoassay system such that the multi-analyte system is no more than a system of n-assays for different n-analytes. This system does not exploit the extreme selectivity shown by the antibodies towards their substrates (similar to that of enzymes towards their own). An improvement to the conventional system and that somehow is reminiscent of how the immune system works is the use of a cocktail of antibodies that will recognize the different analytes, since there will be no cross-reactions between them. This strategy is addressed in the work on a multi-analyte ELISA assay for the detection of different families of antibiotics in milk (Adrian J. et al, Anal and Bioanal Chem, 2008, 391, 1703). Since it involved low-molecular-weight molecules, this required a competitive type assay where the suitable competitor for each analyte had been immobilized separately in the well plate, which allowed obtaining signals separately for each one despite using a mixture of antibodies on the sample. This work demonstrates the possibility of working with mixtures of antibodies without the nonspecific signal being greater than in individual assays and without interference between the responses for different analytes.

DESCRIPTION OF THE INVENTION

The aim of the present invention is an analytical system capable of simultaneously detecting the presence of a single analyte in various samples, or simultaneously detecting the presence of various analytes in a single sample. Accordingly, a high-sensitivity multi-analyte or multi-sample biosensor system is disclosed based on an interdigitated electrode array with barriers, a flow system that combines two types of sample chambers (a multi-cell and a single cell) and a multi-analyte immunoassay by mixing specific antibodies.

The term "analyte" as understood in the present invention is the component to be detected and/or quantified in a sample. In this regard, the analyte may be an element, compound or an ion, i.e. a chemical species that can be detected and/or quantified. A compound is a substance formed by the union of two or more elements of the periodic table, in a fixed ratio. A compound consists of molecules or ions having stable bonds.

Similarly the analyte(s) of interest in a sample can be inorganic, organic or biochemical. The analyte may be biological in nature and therefore could comprise any biological molecule or cell type, cell organelle or any portion thereof. In this sense the term "biological molecule" includes, without limitation, bio-elements (chemicals that appear in living beings), nucleic acids, peptides, proteins, enzymes, carbohydrates, lipids, vitamins, antibodies or hormones.

The analyte of the present invention can be indirectly detected or quantified through the detection or quantification of an antibody capable of specifically recognizing the analyte. This would be the case in which the sample is obtained from an organism whose immune system can generate specific antibodies that recognize the said antigen.

The analyte of the present invention may be present:
In a food sample (veterinary drug residues in animal products, pesticide residues in plant products or microbial contamination).
In a sample of biological origin, more specifically of clinical origin.
In a sample from any environmental compartment (organic compounds of anthropogenic origin, remnants of drugs, pesticides or industrial products).

A first aspect of the invention describes a multiple impedimetric analytical system comprising a multi-electrode chip, a single-duct cell and a second multi-duct cell. The following describes each of these elements.

a) Multi-Electrode Chip

It is a chip comprising an array of microelectrodes whose impedance changes when put in contact with a sample in which a particular analyte is present. Thus, based on the change in impedance of a microelectrode, the amount of analyte present in the sample can be calculated.

In order to describe the multi-electrode chip of the invention, the term "distal end" herein refers to the end on which the microelectrodes are situated, and which is inserted into the groove of the corresponding cell, while the "proximal end" of the multi-electrode chip is the opposite end, which is outside the groove.

In a preferred embodiment of the invention, the distal-end microelectrodes of the multi-electrode chip are electrically connected via conductive tracks to connectors on the proximal end. Both the microelectrodes and the conductive tracks are manufactured using a highly conductive material, preferably $TaSi_2$. Moreover, a dielectric barrier between the microelectrodes avoids short circuits between them, while the tracks, in turn, are coated with a protective dielectric material. In preferred embodiments of the invention, both the dielectric barriers and the coating of the tracks are made of $SiO_2$.

In a preferred embodiment of the invention, the multi-electrode chip is connected through the connectors on its proximal end to an excitation and processing device. The first function of the said excitation and processing device is to cause the passage of a current through the microelectrodes, typically applying a voltage difference between its terminals. Thus, by knowing the voltage difference applied to each microelectrode, the current passed through it will be a ratio of the impedance, which, in turn, is dependent on the amount of analyte present in the sample which has caused the chemical modification of the microelectrode. Therefore, the second function of the excitation and processing medium is to process the intensity signal obtained in order to determine the impedance of each electrode, deducing from the change of this value the amount of analyte present in the sample according to the procedure described later on in this document.

b) Single-Duct Cell

A cell comprising a suitable groove to accommodate the multi-electrode chip and a single duct through which a fluid sample can sequentially flow through each microelectrode of the multi-electrode chip when the latter is inserted in the groove. Preferably, the inlets and outlets of the circulation duct are located on the upper face of the single-duct cell. In short, this cell makes the sample pass through all the electrodes of the multi-electrode chip.

The term "groove" has been used to describe the orifice in which the multi-electrode chip of the invention is inserted because, in a particular embodiment, the multi-electrode chip has a flat and elongated shape. However, the present invention does not intend to limit the shape of the multi-electrode chip, and therefore nor so as regards to the shape of the groove, which may thus be any shape provided it is adapted to house the multi-electrode chip.

c) Multi-Duct Cell

This cell comprises a suitable groove to accommodate the multi-electrode chip and several ducts through which a fluid sample can flow independently through each microelectrode of the multi-electrode chip. As in the case of the single-duct cell, the inlets and outlets of the ducts are preferably located on the upper face of said multi-duct cell. In short, the multi-duct cell allows different samples to pass through each microelectrode without them mixing together.

In preferred embodiments of the invention, each of the preceding cells are fixed between two support plates, forming a "sandwich"-type structure wherein the plates and the cell are joined by screws or by any other system that prevents fluid leakage from the chambers and uncontrolled mixing.

According to a second aspect of the invention, this also discloses a method for the simultaneous detection and/or quantification of various analytes in a single sample, using the multiple impedimetric analytical system described, comprising the following operations:

1) Insert the multi-electrode chip into the groove of the multi-duct cell.

2) Make a suitable compound flow through each of the ducts to achieve the fixing on each microelectrode of a selective receptor or competitor for each analyte to be detected.

3) Remove the multi-electrode chip from the multi-duct cell and insert it into the single-duct cell. After extraction, the multi-electrode chip can be kept for a time in suitable conditions or can be used immediately.

4) Make the sample—mixed with a cocktail of immunoreagents appropriate to each set of analytes to be determined—flow through the duct of the single-duct cell, whereby each of the desired analytes (or the specific antibody) becomes fixed to the relevant activated microelectrode.

In a preferred embodiment of the invention, the difference in the impedance of each microelectrode before and after passage of the sample is used to calculate the analyte concentration.

Thus, before the sample passes through the microelectrodes, a first measurement of the conductivity thereof is performed.

Once the sample has passed sequentially through the electrodes, whereby an analyte (or its antibody) becomes fixed to each microelectrode, a washing solution is passed through the duct of the single-duct cell and then a second measurement of the conductivity of the microelectrodes is performed. The difference in conductivity detected is processed in the excitation and processing device to determine the concentration of each analyte in the sample.

Lastly, a third aspect of the invention discloses a method for the simultaneous detection and/or quantification of a single analyte in various samples by using the multiple impedimetric analytical system. This process comprises the following operations:

1) Insert the multi-electrode chip into the groove of the single-duct cell.

2) Make a suitable compound flow through the single duct to achieve the fixing on each detector electrode of a selective receptor or competitor for the analyte to be detected.

3) Remove the multi-electrode chip from the single-duct cell and insert it into the multi-duct cell. After extraction, the multi-electrode chip can be kept for a time in suitable conditions or can be used immediately.

4) Make the sample (mixed where necessary with the relevant immunoreagent) flow through each duct of the multi-duct cell, whereby the desired analyte (or the complementary antibody) becomes fixed to each microelectrode.

In a preferred embodiment of the invention, the change in the impedance of each electrode before and after passage of the samples is used to calculate the analyte concentration in each sample.

Thus, before the samples pass through the microelectrodes, a first measurement of the impedance thereof is performed.

Once the samples have passed through the microelectrodes, whereby the analyte becomes fixed to each microelectrode, a washing solution is passed through each of the ducts of the multi-duct cell, and then a second measurement of the impedance of the microelectrodes is performed. The difference in impedance detected is processed to determine the analyte concentration in each sample.

DESCRIPTION OF THE FIGURES

To complement the description being made and for the sake of a better understanding of the characteristics of the invention, according to a preferred practical embodiment thereof, a set of drawings is attached as an integral part of said description, drawings which provided by way of illustration and not limiting the scope of this invention appear as follows.

PREFERRED EMBODIMENT OF THE INVENTION

Described below is an example of a multiple impedimetric analytical system according to the present invention, with reference to the accompanying figures. In particular, it is an analytical system suitable for performing four parallel tests either to determine four different compounds in the same sample or the same compound in four different samples.

Figure 1:
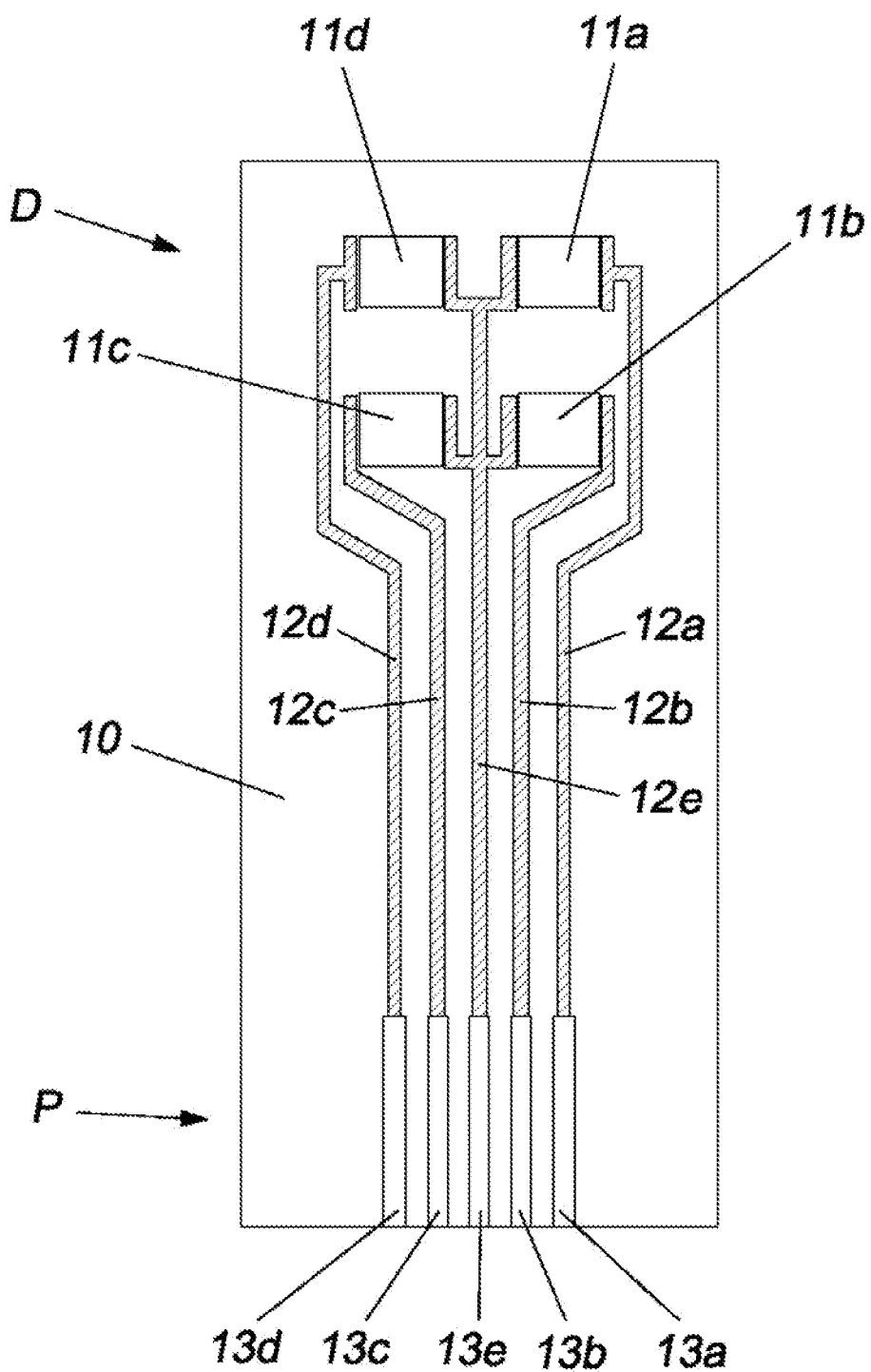
FIG. 1.—Shows a plan view of a multi-electrode chip according to the present invention.

FIG. 1 shows a tetra-electrode chip (10), at whose distal end (D) four microelectrodes (11a, 11b, 11c, 11d) are shown which are linked electrically by means of four conductive tracks (12a, 12b, 12c, 12d) to metal connectors (13a, 13b, 13c, 13d, 13e) located at the proximal end (P). In this example, the microelectrodes (11a, 11b, 11c, 11d) are made of tantalum silicide ($TaSi_2$), and dielectric barriers (not shown in the figures) have been built between them to minimize the risk of short circuiting.

Furthermore, it can be seen how the microelectrodes (11a, 11b, 11c, 11d) have a shared terminal (12e) attached to the connector (13e), which serves as a reference when applying the voltage required to measure the impedance of each one.

Figure 2A:
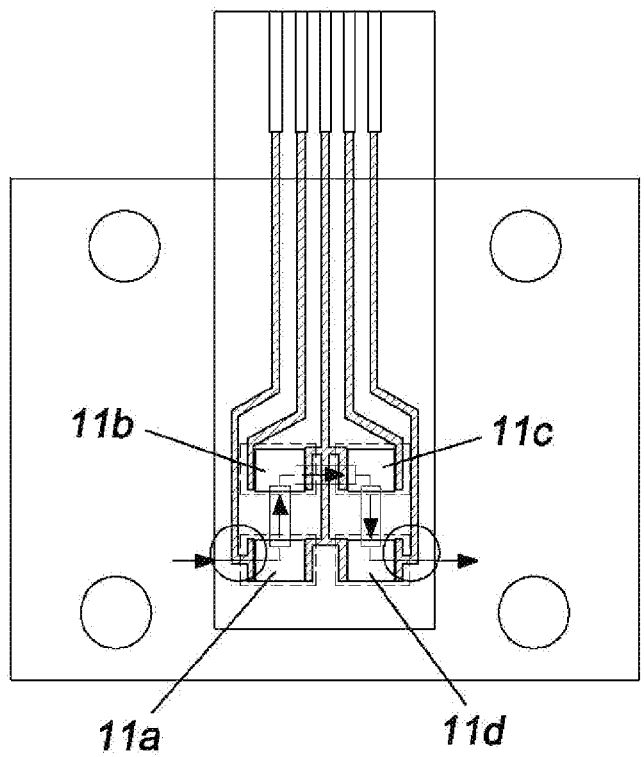
FIGS. 2a and 2b.—Show both plan and elevation views of the multi-electrode chip of the invention inserted in the groove of a single-duct cell.
Figure 2B:
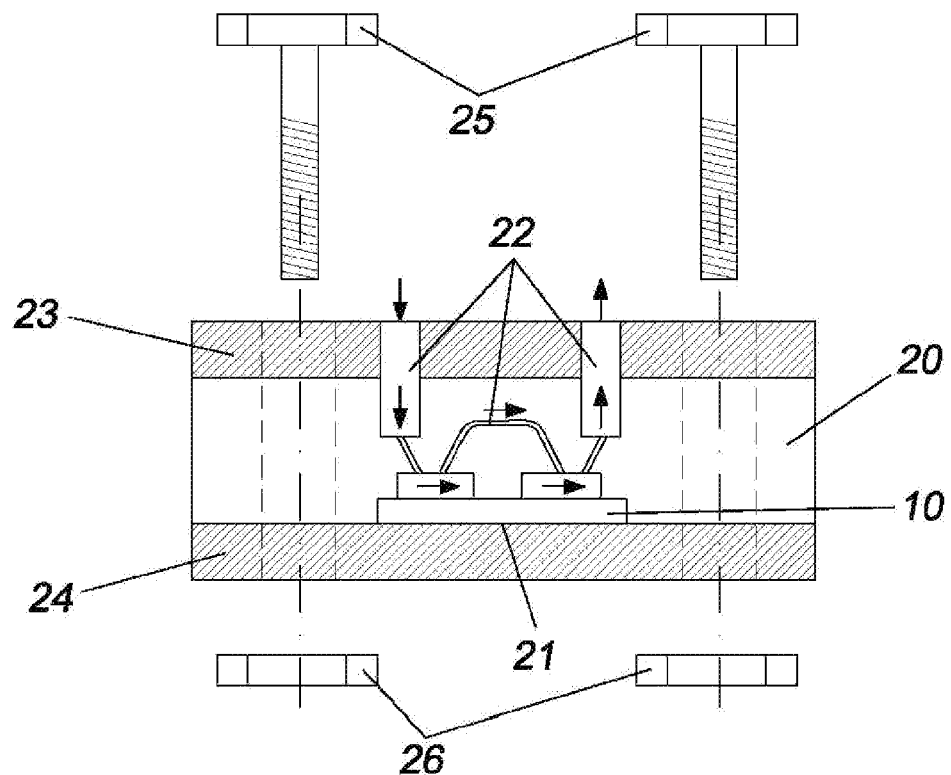

FIGS. 2a and 2b show the tetra-electrode chip (10) inserted in the groove (21) of the single-duct cell (20). In this example, the duct (22) has an inlet orifice located on the upper face of the cell (20), stretching vertically downwards to the first of the microelectrodes (11a) and then passing sequentially in the direction indicated by the arrows through the microelectrode (11b), through the microelectrode (11c) and through the microelectrode (11d). Finally, the duct (22) again stretches vertically upwards to the outlet orifice. Thus, in a single operation the same fluid can be circulated through the four microelectrodes (11a, 11b, 11c, 11c).

FIG. 2b also shows how the single-duct cell (20) is enclosed between two support plates (23, 24) and is secured between them by screws (25) and nuts (26).

Figure 3A:
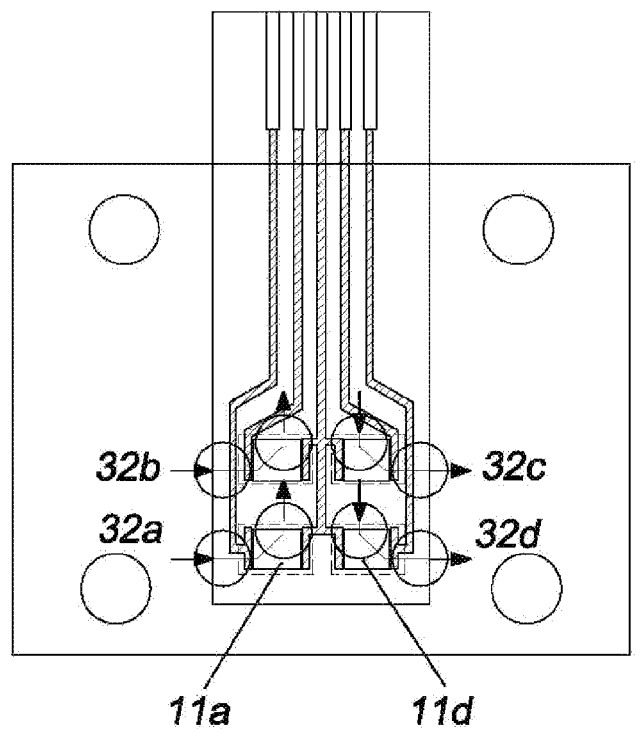
FIGS. 3a and 3b.—Show both plan and elevation views of the multi-electrode chip (namely the four-electrode model) of the invention inserted in the groove of a multi-duct cell.
Figure 3B:
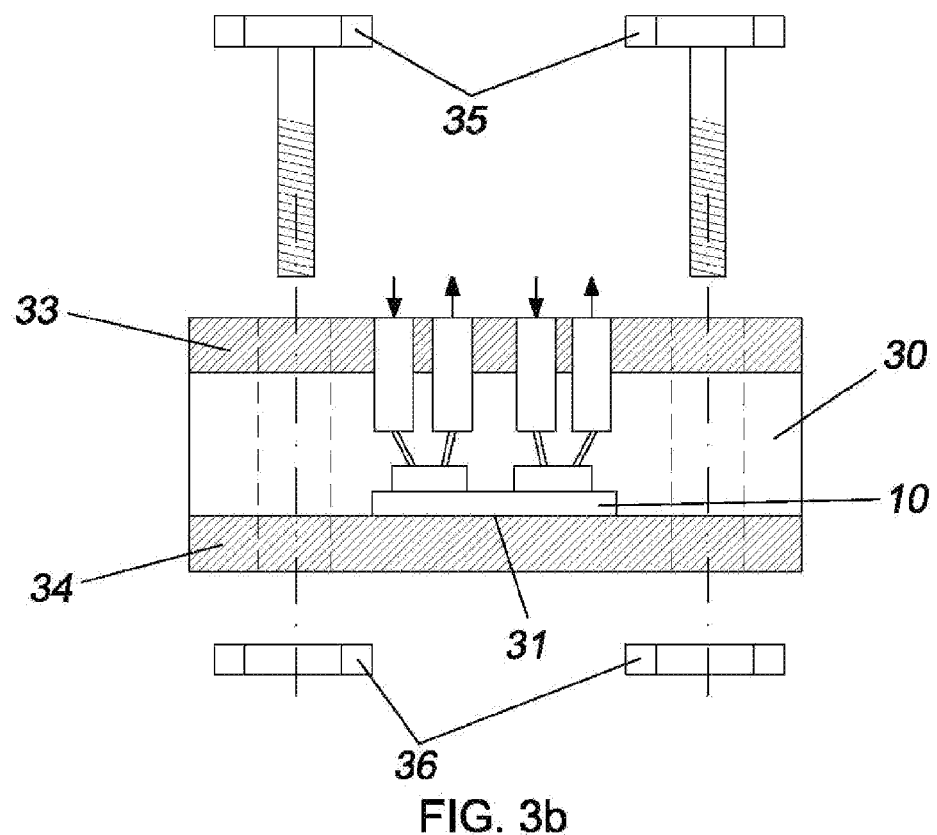

FIGS. 3a and 3b show the tetra-electrode chip (10) inserted in the groove (31) of the second multi-duct cell (30). In this case, four independent ducts (32a, 32b, 32c, 32d) can be seen, each of which descends vertically from their respective inlets to each microelectrode (11a, 11b, 11c, 11d), then rising to their outlets. Thus, four different fluids can circulate simultaneously, each one through one of the microelectrodes (11a, 11b, 11c, 11d).

The second cell (30) is also fixed between two support plates (33, 34) by screws (35) and nuts (36).

Example

In a first example, the simultaneous detection and/or quantification of multiple analytes in a single sample using the system of the invention is intended. In particular, it is sought to know if a food sample is contaminated by atrazine (ATRZ), azinphos (AZM), trichlorophenol (TCP) or bromopropylate (BP) pesticides which we shall call the problem analytes.

To do this, firstly the tetra-electrode chip (10) was introduced (step 1) into the groove (31) of a multi-duct cell (30) and a solution for washing and activating the electrode surface was passed through each duct (32a, 32b, 32c, 32d). Then one proceeds with the phase of immobilization on an insoluble support which involves passing a specific antigen for each analyte (AT1, AT2, AT3 and AT4), in order to selectively immobilize them (step 2) on the surface of each microelectrode (11a, 11b, 11c, 11d).

The immobilization of compounds on the surface of a support such as one of the microelectrodes (11a, 11b, 11c, 11d) of this invention is directed by the chemistry of the surface. There are many factors that can change the ability of immobilization of the compounds. The incubation time and temperature are very important. Generally, the higher the temperature less is the incubation time required but it is preferable to use a temperature of between 3 and 6° C. for a time of between 10 and 20 hours to immobilize the compounds on the solid support surface.

The antigen immobilization step includes a final step involving the blocking of the support spaces not occupied by the antigen, as binding thereto is not selective and if blocking is not carried out other nonspecific molecules could bind. Blocking was carried out by using proteins or detergents, preferably non-ionic detergents. More preferably PBST is used.

PBS is a phosphate buffer of 10 mM, with 0.8% of saline solution, and if not otherwise stated the pH is 7.5. The PBST is PBS with Tween 20 at 0.05%. The coating buffer is 0.05 M carbonate-bicarbonate, pH 9.6.

A PBST wash solution is then passed through each duct (32a, 32b, 32c, 32d) to remove those antigens that were not attached to the microelectrode (11a, 11b, 11c, 11d).

The multi-electrode chip (10) was then extracted from the groove (31) of the multi-duct cell (30). This activated and functionalized electrode can be stored in cold conditions and an inert atmosphere for later use. Up to this point, it can be considered as the sensor construction and preparation phase.

For the measurement step, the corresponding activated and functionalized chip was inserted in the groove (21) of the single-duct cell (20) (step 3). The mixture of the sample with the anti-antigen antibodies (Ac1, Ac2, Ac3 and c4) for the four analytes to be detected, pre-incubated for a certain time, was passed through the duct (22) of the single-duct cell (20) (step 4). The fraction of antibodies which has not reacted with the analyte present in the sample will be bound to the functionalized microelectrode with the corresponding antigen (11a, 11b, 11c, 11d).

Pre-incubation consisted of mixing the sample and anti-antigen antibodies for a given time, preferably less than 30 minutes, at a temperature of between 15° C. and 30° C. The pre-incubated mixture was passed through antigens immobilized on the microelectrodes (11a, 11b, 11c, 11d) and incubated under the same conditions as the pre-incubation for a time of between 5 and 15 minutes. Thus the binding of the free antibodies that may remain in the sample to the antigen immobilized on the support was obtained.

The next step was to wash the microelectrodes (11a, 11b, 11c, 11d) to eliminate those substances which had not specifically bound to the immobilized antigens as described.

Figure 4:
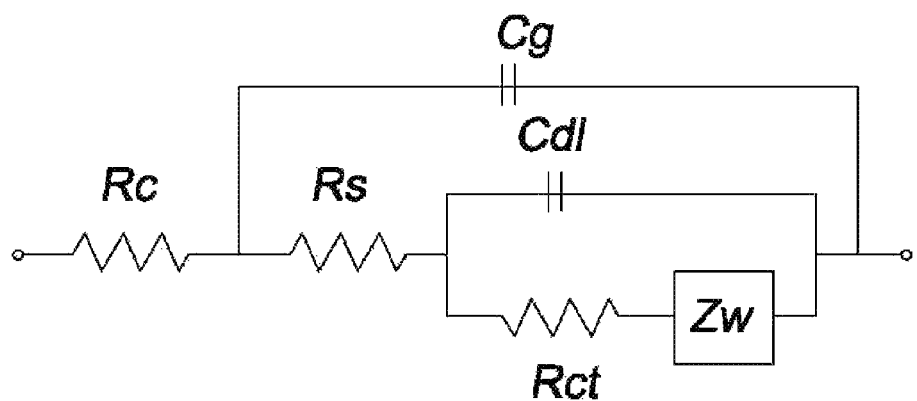
FIG. 4.—Shows the equivalent circuit used for adjusting the experimental values of impedance.
Figure 5A:
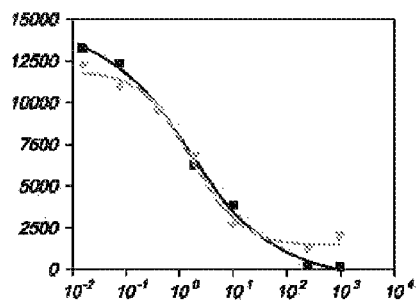
FIG. 5.—Shows the calibration curves made with the immunoreagents corresponding to each analyte and with the "cocktail" solution containing all the antibodies from each of the analytes used in the example of the present invention.
Figure 5B:
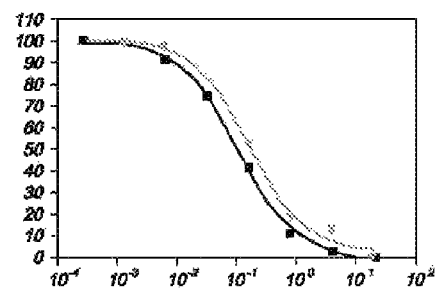
Figure 5C:
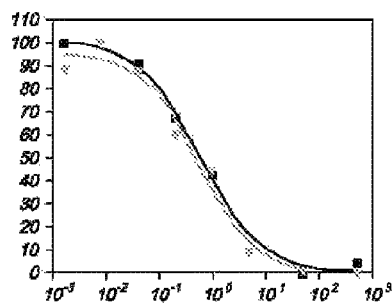
Figure 5D:
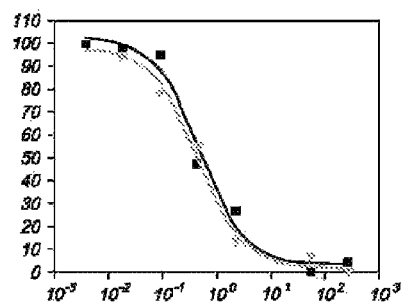

Then, a measuring solution was passed through each duct (32a, 32b, 32c, 32d) such that the microelectrodes (11a, 11b, 11c, 11d) are submerged. The measuring solution is a solution of KCl 1×10⁻⁶ M, with a conductivity of 1.6 $\mu Scm^{-1}$. Impedance measurements were taken in the frequency range between 100 kHz and 10 Hz. Impedance data obtained were adjusted to the equivalent circuit presented in FIG. 4 using the commercial software: Zplot/Zview (Scribner Associates Inc.).

Impedance measurements were compared with control impedance measurements to determine the analyte concentration in the sample.

The control is a group of solutions containing the analyte to be detected and/or quantified in the present invention, at known concentrations, so that the impedance values and the concentration values maintain a known ratio in a given range making it possible to create a calibration or linear regression curve (FIGS. 5a, 5b, 5c and 5d). The concentrations of the compound present in the sample are quantified by interpolating the values obtained in the measurement preferably in linear area of the calibration curve or linear regression line.

TABLE 1

Concentration range used for the calibration curves.

| Assay | Calibration curves interval (μgL−1) |
| --- | --- |
| Atrazine | 500-1.6 × 10−3 |
| TCP | 200-3 × 10−3 |
| Bromopropylate | 250-4 × 10−3 |
| Azinphos | 300-3.84 × 10−3 |

In addition, a first conductivity measurement of the microelectrodes (11a, 11b, 11c, 11d) was performed prior to passage of the samples through said microelectrodes (11a, 11b, 11c, 11d) using only the detection buffer. This measurement is the reference measurement to be subtracted from the measurements obtained in the second measurement to determine the actual measurement of the impedance variation due solely to the presence of the analyte. A second conductivity measurement of the microelectrodes (11a, 11b, 11c, 11d) was carried out after the samples has passed through said microelectrodes (11a, 11b, 11c, 11d) and after a subsequent washing stage as described above.

The invention claimed is:

1. A multiple multi-analyte system based on impedimetric measurements for simultaneous detection and/or quantification of various analytes in a single sample or for the simultaneous detection of an analyte in various samples, comprising:
    a multi-electrode chip comprising a set of microelectrodes;
    a single-duct cell, comprising a groove suitable for accommodating the multi-electrode chip and a single duct through which a fluid sample can sequentially flow through each of the microelectrodes of a multi-electrode chip when the latter is inserted in the groove;
    a second multi-duct cell, comprising a groove suitable for accommodating the multi-electrode chip and several independent ducts through which various fluid samples can flow independently through each microelectrode of the multi-electrode chip.

2. The system of claim 1, further comprising an excitation and processing device connected to the multi-electrode chip.

3. The system of claim 2, wherein the microelectrodes located at a distal end (D) of the multi-electrode chip, are electrically connected by means of tracks to connectors, located at a proximal end (P), which allow the connection of said multi-electrode chip to the excitation and processing device.

4. The system of claim 3, wherein the microelectrodes and tracks are made of $TaSi_2$.

5. The system of claim 1, further comprising dielectric barriers separating the microelectrodes from each other.

6. The system of claim 3, further comprising a dielectric coating to protect the tracks.

7. The system of claim 5, wherein the dielectric barriers are made of $SiO_2$.

8. The system of claim 6, wherein the dielectric coating is made of $SiO_2$.

9. The system of claim 1, wherein each cell is fixed to two support plates, forming a "sandwich"-type structure.

10. A method for the simultaneous detection and/or quantification of various analytes in a single sample comprising the following operations:
    inserting a multi-electrode chip in a groove of a multi-duct cell;
    making a suitable compound flow through several ducts to achieve the fixing on each microelectrode of a selective receptor or competitor for each analyte to be detected;
    removing the multi-electrode chip from the multi-duct cell and insert it into a groove of a single-duct cell;
    making the single sample mixed with a cocktail of inmunoreagents appropriate to each analyte flow through a duct of the single-duct cell, whereby each of the desired analytes becomes fixed to the corresponding microelectrode;
    performing a first measurement of the conductivity of the microelectrodes prior to the passage of the sample through such microelectrodes;
    performing a second measurement of the conductivity of the microelectrodes after the passage of the sample through said microelectrodes and a subsequent washing stage; and
    determining, based on the two preceding measurements, the amount of each analyte in each microelectrode.

11. A method for the simultaneous detection and/or quantification of a single analyte in various samples comprising the following operations:
    inserting a multi-electrode chip in a groove of a single-duct cell;
    making a suitable compound flow through a duct to achieve the fixing on each microelectrode of a selective receptor or competitor for the analyte to be detected;
    removing the multi-electrode chip from the single-duct cell and insert into a groove of a multi-duct cell;
    making a sample flow through each duct of the multi-duct cell, whereby the desired analyte becomes fixed to each microelectrode;
    performing a first measurement of the conductivity of the microelectrodes prior to the passage of the samples through such microelectrodes;
    performing a second measurement of the conductivity of the microelectrodes after the passage of the samples through said microelectrodes and a subsequent washing stage; and
    determining, based on the two preceding measurements, the amount of analyte in each microelectrode.

* * * * *